(12) United States Patent
Hathaway, Jr. et al.

(10) Patent No.: US 9,044,733 B2
(45) Date of Patent: Jun. 2, 2015

(54) METHOD AND APPARATUS FOR PREPARING A SOLUTION OF A SHEAR SENSITIVE MATERIAL

(75) Inventors: Royal D. Hathaway, Jr., Montgomery Village, MD (US); Joseph R. Sclafani, Jr., Penn Valley, PA (US)

(73) Assignee: Otsuka America Pharmaceutical, Inc., Rockville, MD (US)

( * ) Notice: Subject to any disclaimer, the term of this patent is extended or adjusted under 35 U.S.C. 154(b) by 1061 days.

(21) Appl. No.: 12/467,608

(22) Filed: May 18, 2009

(65) Prior Publication Data

US 2009/0287021 A1    Nov. 19, 2009

Related U.S. Application Data

(60) Provisional application No. 61/071,812, filed on May 19, 2008.

(51) Int. Cl.
*B01J 19/18* (2006.01)
*C07C 279/26* (2006.01)

(52) U.S. Cl.
CPC ........... *B01J 19/1881* (2013.01); *C07C 279/26* (2013.01)

(58) Field of Classification Search
USPC .................................................. 422/132, 129
See application file for complete search history.

(56) References Cited

U.S. PATENT DOCUMENTS

| | | | | |
|---|---|---|---|---|
| 4,670,150 | A | * | 6/1987 | Hsiung et al. .................. 210/636 |
| 5,811,259 | A | * | 9/1998 | Hall ................................ 435/41 |
| 2002/0043487 | A1 | | 4/2002 | Schick |
| 2007/0041866 | A1 | | 2/2007 | Miyata et al. |

FOREIGN PATENT DOCUMENTS

| | | |
|---|---|---|
| EP | 1 634 589 A1 | 3/2006 |
| JP | 2005-289959 A | 10/2005 |
| WO | WO 90/15082 | 12/1990 |
| WO | WO 99/25319 | 5/1999 |
| WO | WO 99/57300 | 11/1999 |

OTHER PUBLICATIONS

English-language abstract of JP 2005-289959 A, published on Oct. 20, 2005.

* cited by examiner

*Primary Examiner* — Natalia Levkovich
(74) *Attorney, Agent, or Firm* — Finnegan, Henderson, Farabow, Garrett & Dunner LLP

(57) ABSTRACT

The invention provides a novel apparatus and method for preparing a solution of a shear sensitive material.

18 Claims, 8 Drawing Sheets

Figure 1: A flow chart of the conventional manufacturing process.

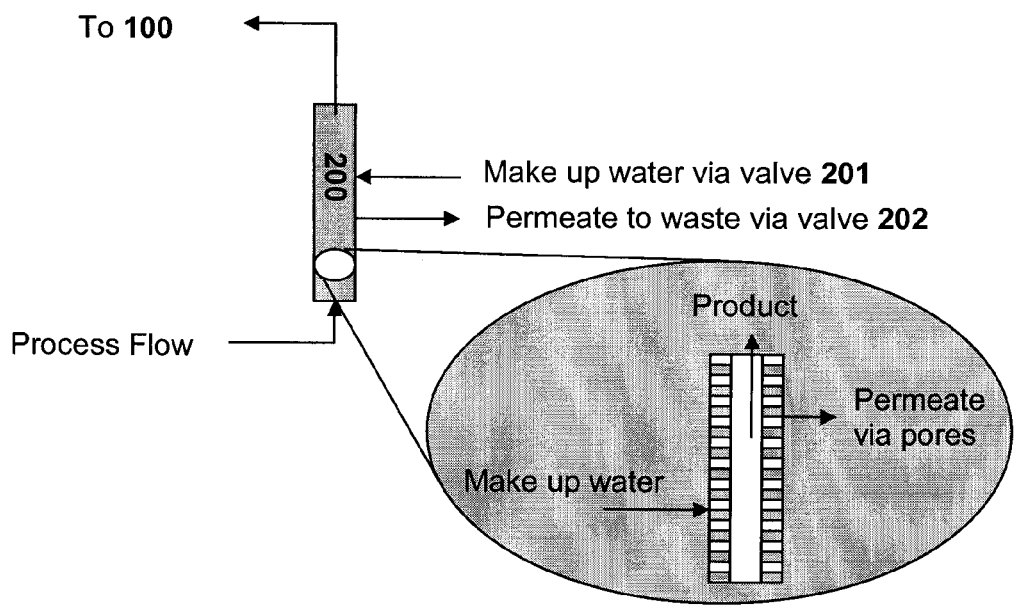
Figure 4: A schematic diagram illustrating the continuous diafiltration system.

METHOD AND APPARATUS FOR PREPARING A SOLUTION OF A SHEAR SENSITIVE MATERIAL

This application claims priority to U.S. Provisional Application No. 61/071,812, filed on May 19, 2008, the disclosure of which is incorporated by reference herein.

DESCRIPTION OF THE INVENTION

1. Field of the Invention

The present disclosure generally relates to an apparatus and method for preparing a solution of a shear sensitive material. In one embodiment, the novel process prepares an aqueous solution containing $N^1$-(3,4-dichlorobenzyl)-$N^5$-octyl-biguanide (olanexidine) gluconate.

2. Background of the Invention

In a conventional manufacturing process, preparing a solution of a shear sensitive material from an initial slurry that requires filtration to remove unwanted impurities offers various disadvantages. For example, agitation of the starting slurry in the process vessel can create decreased particle size which can then clog the pores of the filter unit. In addition, filtering the slurry using a traditional filtration system where the product feed stream flows through the pores of the filter can produce a low permeate flow rate and clogged pores.

In the conventional manufacturing process, the layout of the equipment is variable, but typically some of the equipment required to produce a large batch of a solution of a shear sensitive material is permanently installed in the process facility. The filter unit may be located below the slurry vessel so that gravity can aid in draining the contents onto the filter. All of the equipment used in the conventional manufacturing process requires the appropriate ancillary support functions in addition to water, electricity, and pressurized gas. In addition, cleaning all of the individual units requires manual intervention. In fact, each of the batch operations used in the conventional manufacturing process requires manual input and/or manual transfer.

For example, in the conventional manufacturing process, an aqueous solution of $N^1$-(3,4-dichlorobenzyl)-$N^5$-octyl-biguanide gluconate concentrate is typically produced by performing multiple individual operations as a series of manual batch processes. FIG. 1 shows the steps of the conventional manufacturing process, comprising a desalting process and a solubilization process.

In the desalting process, sodium hydroxide is added to a vessel containing an aqueous slurry of $N^1$-(3,4-dichlorobenzyl)-$N^5$-octyl-biguanide hydrogen chloride salt to generate the free base, also as a slurry. This free base slurry is then transferred to a filtration unit where the sodium hydroxide and liberated chloride are removed in the filtrate. To insure adequate removal, the process of resuspending the resulting free base cake in water and refiltering is repeated multiple times. The washed wet free base cake is then harvested.

In the solubilization process, the free base is added to a clean vessel containing an aqueous solution of the surfactant, poloxamer (Pluronic™). This is performed by manually scooping the wet cake into the reactor vessel via an appropriate opening (manway, etc.) or by first suspending the free base in water as a slurry and pulling it into the reactor under vacuum or motivated by a pump. Gluconic acid (glucono-δ-lactone solution) is then added, causing the slurry to dissolve to form a transparent solution. After a volume adjustment, samples are withdrawn for pH measurement and the pH is adjusted manually by adding the appropriate amount of acid or base. Thereafter, samples are pulled for quantification and a calculated amount of water is added to the solution to achieve the targeted $N^1$-(3,4-dichlorobenzyl)-$N^5$-octyl-biguanide gluconate concentration. After the solution is passed through a 0.45 μm clarification filter, it is ready for testing and further processing into product.

For a large scale process, however, an automated process in a self-contained process unit offers advantages over the conventional manufacturing process. These advantages can include portability, automation, a fully contained system that requires minimal handling and minimizes manual human intervention, controlled chemical introduction, and an automated mechanism for cleaning the self-contained process unit without disassembly of the unit.

Many of the advantages of the automated self-contained process result from the recirculating nature of the process. The self-contained process unit allows for a circulating stream of materials within the unit. In addition, the circulating nature permits other chemicals required of the process to be introduced via one or more pumps into the circulating process stream.

Moreover, a circulating process stream permits the continuous filtration of the desired product using a tangential flow filtration system through at least one filter. To maintain an adequately high permeate flow rate through the tangential flow filters, filters can be added in series. As compared to using a single filter, it was anticipated that placing two filters in series would result in a permeate flow rate of less than double and that placing three filters in series would result in a permeate flow rate of less than triple. Surprisingly, it was discovered that the permeate flow rates were more than double for two filters in series and more than triple for three filters in series.

In addition, a tangential flow filtration system where the particles (retentate) flow over the filter and the liquid (permeate) passes through the hollow membranes of the filter unit allows a back-flush flow of clean liquid through the filter to dislodge particles and to replace the volume of liquid lost as the permeate stream. Accordingly, the present invention is directed to addressing one or more of the needs described above.

SUMMARY OF THE INVENTION

The present invention concerns a novel apparatus and method for preparing a solution of a shear sensitive material. In one embodiment, the novel process prepares an aqueous solution containing $N^1$-(3,4-dichlorobenzyl)-$N^5$-octyl-biguanide (olanexidine) gluconate.

In one aspect, the invention relates to an apparatus for preparing a solution of a shear sensitive material comprising:
 a process vessel comprising an inlet for adding dry ingredients, an agitator, a dip tube, and a outlet valve;
 a first pump connected to the outlet valve;
 at least one tangential flow filter connected to both the first pump and the dip tube of the process vessel wherein the process vessel, the first pump, and the at least one tangential flow filter are configured to form a circulating loop; and
 at least one addition tank and at least one addition pump wherein the addition pump is configured to pump a reagent from the addition tank into the circulating loop.

In another aspect, the invention relates to a process for preparing a solution of a shear sensitive material comprising:
 a) adding a liquid to a shear sensitive material to form a slurry;
 b) adding a first reagent to the slurry wherein the first reagent changes the properties or composition of the slurry;

c) passing the slurry containing the shear sensitive material through at least one tangential flow filter;

d) separating a filtrate from the slurry as a permeate stream by filtration;

e) adding a liquid to the slurry in an amount to replace at least some of the volume of liquid lost as the permeate stream; and f) adding a second reagent to the slurry wherein the second reagent changes the solubility of the shear sensitive material to yield a solution.

In another aspect, the invention relates to a process for preparing olanexidine gluconate comprising:

a) adding an aqueous base to an aqueous slurry of a salt of olanexidine;

b) passing the slurry containing olanexidine through at least one tangential flow filter;

c) separating a filtrate from the slurry of olanexidine as a permeate stream by filtration;

d) adding water to the slurry of olanexidine in an amount to replace at least some of the volume of water lost as the permeate stream; and e) adding a glucono-δ-lactone (gluconic acid) solution to the slurry of olanexidine to yield a first aqueous solution of olanexidine gluconate.

In another aspect, the invention relates to a process for preparing olanexidine gluconate comprising:

a) adding an aqueous sodium hydroxide solution to a first aqueous slurry of olanexidine hydrochloride;

b) passing the slurry containing olanexidine through at least one tangential flow filter;

c) separating a filtrate from the slurry of olanexidine as a permeate stream by filtration;

d) adding water to the slurry of olanexidine in an amount to replace at least some of the volume of water lost as the permeate stream;

e) adding a surfactant solution to the slurry of olanexidine to yield a second aqueous slurry; and f) adding a glucono-δ-lactone (gluconic acid) solution to the second aqueous slurry to yield a first aqueous solution of olanexidine gluconate.

In another aspect, the invention relates to a process for preparing olanexidine gluconate comprising:

a) adding an aqueous sodium hydroxide solution to a first aqueous slurry of olanexidine hydrochloride;

b) passing the slurry containing olanexidine through at least one tangential flow filter;

c) separating a filtrate from the slurry of olanexidine as a permeate stream by filtration;

d) adding water to the slurry of olanexidine in an amount to replace at least some of the volume of water lost as the permeate stream;

e) adding a poloxamer solution to the slurry of olanexidine to yield a second aqueous slurry;

f) adding a glucono-δ-lactone (gluconic acid) solution to the second aqueous slurry to yield a first aqueous solution of olanexidine gluconate; and g) adding water to the first aqueous solution to yield a second aqueous solution of olanexidine gluconate with a concentration ranging from about 0.1% to about 75% (W/V).

Additional objects and advantages of the invention will be set forth in part in the description which follows, and in part will be obvious from the description, or may be learned by practicing the invention. The objects and advantages of the invention will be realized and attained by means of the elements and combinations particularly pointed out in the appended claims.

The accompanying drawings, which are incorporated in and constitute a part of this specification, illustrate several embodiments of the invention and together with the description, serve to explain the principles of the invention.

It is to be understood that both the foregoing general description and the following drawings and detailed description are exemplary and explanatory only and are not intended to limit the invention, as claimed.

BRIEF DESCRIPTION OF THE DRAWINGS

FIG. 4 illustrates the continuous tangential flow filtration system of FIG. 2.

DESCRIPTION OF THE EMBODIMENTS

Figure 1:
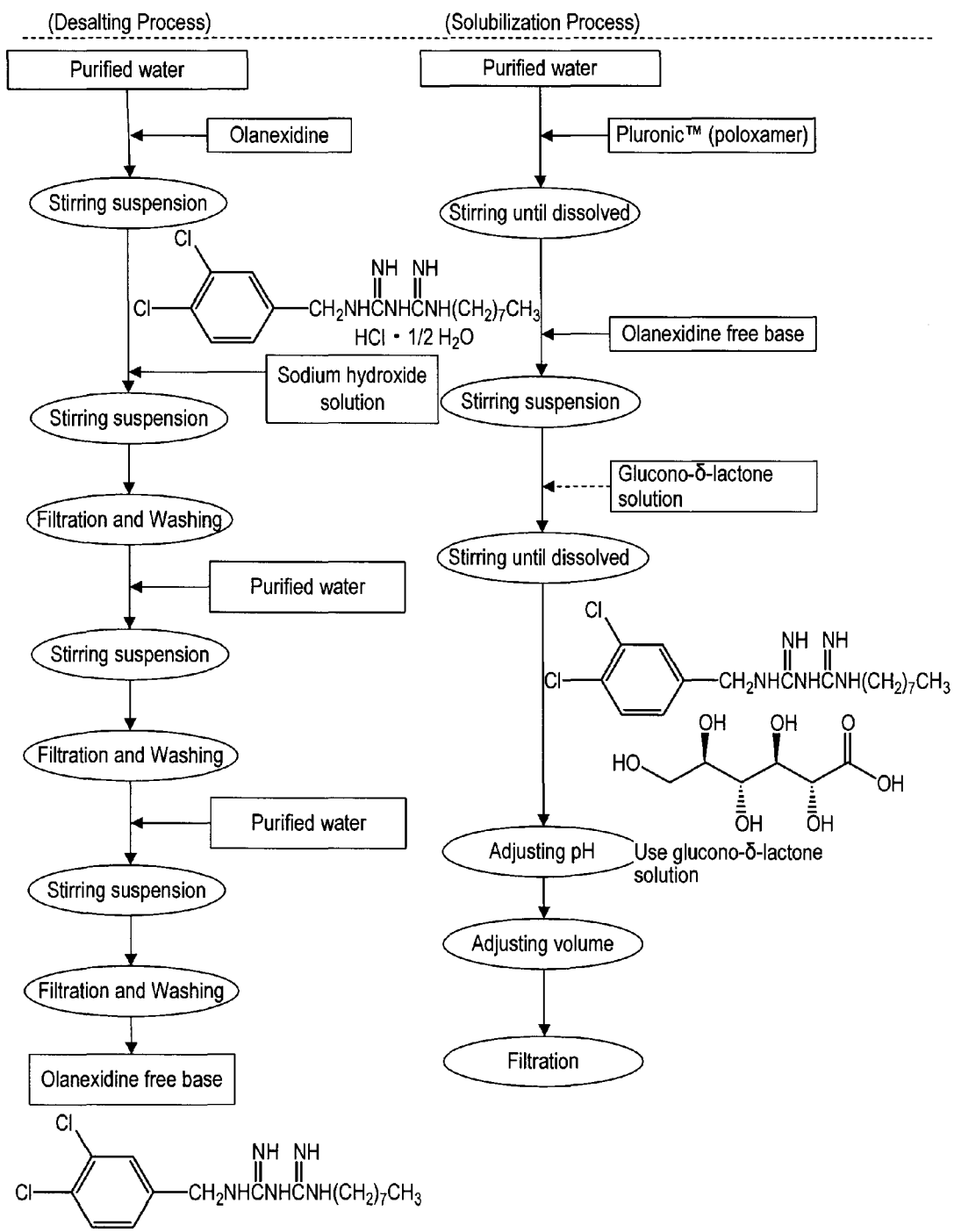
FIG. 1 is a flow diagram showing the steps of the conventional manufacturing process for $N^1$-(3,4-dichlorobenzyl)-$N^5$-octyl-biguanide gluconate, comprising a desalting process and a solubilization process.

The present disclosure may be understood more readily by reference to the following detailed description of certain embodiments of the invention and the working examples.

In accordance with the purposes of this invention, certain embodiments of the invention are described in the Summary of the Invention and are further described below. Also, other embodiments of the invention are described herein.

Unless otherwise indicated, all numbers expressing quantities of ingredients, properties, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all numbers between 0 and 10 such as, for example, 1, 2, 3, 4, etc., as well as the endpoints 0 and 10.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation of the respective measurements.

As used in the specification and the appended claims, the singular forms "a," "an," and "the" include their plural referents unless the context clearly dictates otherwise. For example, reference to the processing or filtering of "a slurry," is intended to include the processing or filtering of a plurality of slurries. Likewise, references to a composition containing or including "a" given component or product is intended to include other ingredients or other components or products, in addition to the one named.

By "comprising" or "containing" or "including" we mean that at least the named compound, element, particle, or method step, etc., is present in the composition or article or method, but we do not exclude the presence of other compounds, catalysts, materials, particles, method steps, etc., even if the other such compounds, materials, particles, method steps, etc., have the same function as what is named, unless expressly excluded by the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and does not necessarily imply a particular order of adding ingredients or performing steps.

The term "approximately," as used herein, is intended to have the same meaning as "about."

The term "continuous," as used herein, describes a process in which there is a circulating process stream from the tank through the at least one tangential flow filter back to the tank. The continuous process contrasts with a batch process wherein filtration would take place as a series of individual unit operations of suspending the slurry, filtering, washing and harvesting, some or all of which the operator may have to perform multiple times.

The term "clean-in-place," as used herein, describes a mechanism, which can be automated, for cleaning the self-contained process unit without disassembly of the unit. The term is abbreviated as "CIP."

The term "diafiltration," as used herein, describes a tangential flow filtration process whereby undesirable species are washed out of the recirculating product slurry into the permeate stream.

In the specification and claims, the concentration of each ingredient in an aqueous solution is, unless otherwise indicated, expressed as a weight per volume percentage "% (W/V)", i.e., the weight (kg) of each ingredient/1 L of the aqueous solution multiplied by 100. The abbreviation "kg" represents the weight in kilograms and the abbreviation "L" represents the volume in liters.

As used herein, the abbreviation (w/w) indicates a weight by weight solution.

The solution of a shear sensitive material can be, for example, an antiseptic solution containing an active ingredient. Various antiseptic solution active ingredients are known in the art, including, but not limited to, benzalkonium chloride; benzethonium chloride; chlorhexidine gluconate; chlorhexidine gluconate with alcohol; chloroxylenol; cloflucarban; fluorosalan; hexachlorophene; hexylresorcinols; iodine-containing compounds; povidone iodine; povidone iodine with alcohol; and combinations thereof.

In certain embodiments, the antiseptic solution may include a biguanide derivative and/or salts thereof, e.g., olanexidine [$N^1$-(3,4-dichlorobenzyl)-$N^5$-octyl-biguanide] and salts thereof, as the active ingredient, as disclosed, for example in U.S. Pat. No. 5,376,686. U.S. Pat. No. 5,376,686 discloses methods for preparing salts of olanexidine, which methods are incorporated by reference. These salts of olanexidine include hydrochloride, lactate, glycolate, monomethanesulfonate, hydrobromade, phosphate, dimethanesulfonate, and dihydrochloride salts.

The liquid comprising a slurry and/or solution of shear sensitive material may be an organic solvent or water. In certain embodiments, the liquid is water. In other embodiments, the organic solvent can include, but is not limited to, ethanol, isopropyl alcohol, other alcohols, and combinations thereof.

In certain embodiments, the solution of a shear sensitive material may be prepared in various concentrations. For example, in certain embodiments, the shear sensitive material may be present at a concentration ranging from about 0.1% to about 75% (W/V of shear sensitive ingredient). In certain embodiments, the concentration of the shear sensitive material can be about 0.1% to about 50%; about 0.1% to about 25%; about 0.1% to about 20%; about 0.1% to about 15%; and about 0.1% to about 10% (W/V of shear sensitive ingredient).

The solution of a shear sensitive material may also incorporate certain surfactants, for example, polyoxyethylene-based nonionic surfactants, sorbitans, polysorbates, polyoxyl-alkane-surfactants, ionic surfactants, for example, sodium lauryl sulfate, and/or alcohols, for example, ethanol, isopropyl alcohol and other alcohols, and/or water, in varying amounts. Useful surfactants are known to one skilled in the art, for example, Poloxamer 124 (a/k/a Polyoxypropylene-polyoxyethylene Block Copolymer 124), which is available from BASF and is also referred to as Pluronic L44, POE (9) lauryl ether (available as 'BL-9EX' from Nikko Chemicals Co., Ltd., Tokyo, Japan), POE (10) lauryl ether, also known as nonoxynol-10, or NP-10, (available as 'Emulin NL-100' from Sanyo Chemical Industries, Ltd., Kyoto Japan).

With reference now to the drawings, an apparatus for use in preparing a solution of a shear sensitive material in accordance with some embodiments of the present invention is illustrated in FIGS. 2, 2A, 2B, and 2C in a generalized block format.

In one aspect of the invention, the apparatus is a self-contained process unit containing a tank 100, connected to a pump 150. The pump 150 can pump the slurry containing the shear sensitive material through a filtration system 200, which then connects back to the tank 100, forming a circulating process stream. The addition system 300 permits a desired reagent to be pumped by pump 301 into the circulating process stream. In some embodiments, a desired reagent can be pumped into the circulating process stream after the process stream passes through the filtration system 200. In some embodiments, a desired reagent can be pumped into the circulating process stream before the process stream passes through the filtration system 200. In certain embodiments, process water 50 can be added to the tank 100 via valve 51. In certain embodiments, process water 50 can be added to the filtration system 200 via valve 201. The addition of water directly through the filtration system 200 allows a back-flush flow of purified water through the pores of the filter to dislodge particles while replacing the volume of liquid lost as the permeate stream.

Once a solution of a shear sensitive material is prepared, valve 120 in the circulating process stream can be opened to allow transfer of the solution to a connected transfer tank 400. In certain embodiments, the solution can pass through filter 401 to clarify the solution before entering the transfer tank. In certain embodiments, the transfer tank can include wheels.

Figure 2:
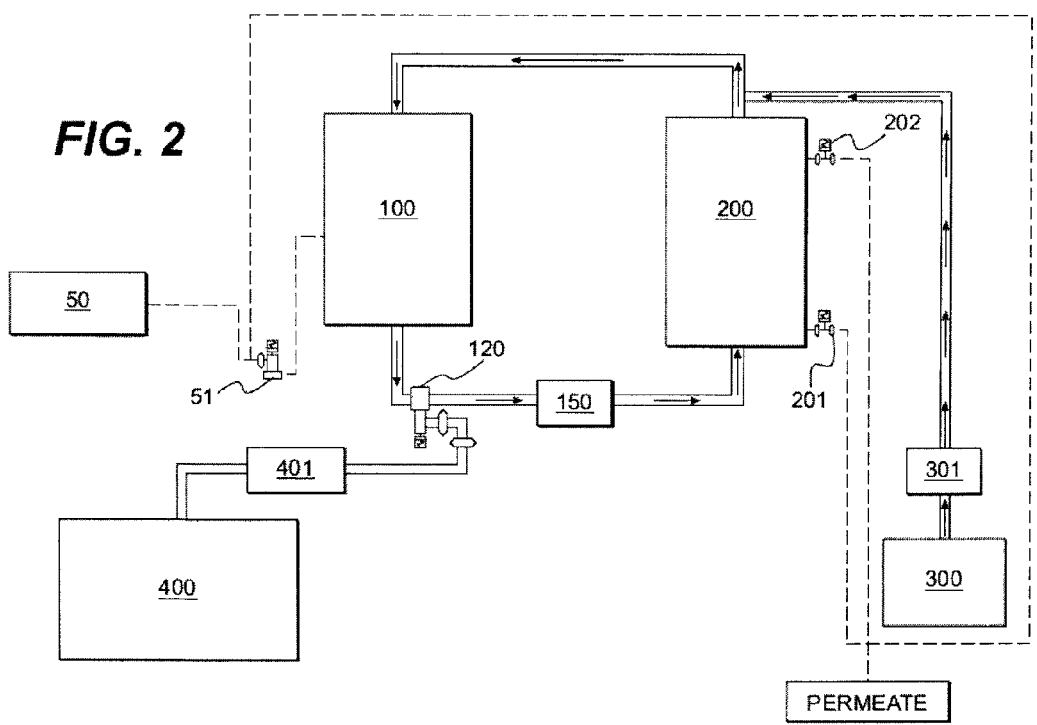
FIG. 2 illustrates a manufacturing apparatus according to an embodiment of the present invention.
Figure 3:
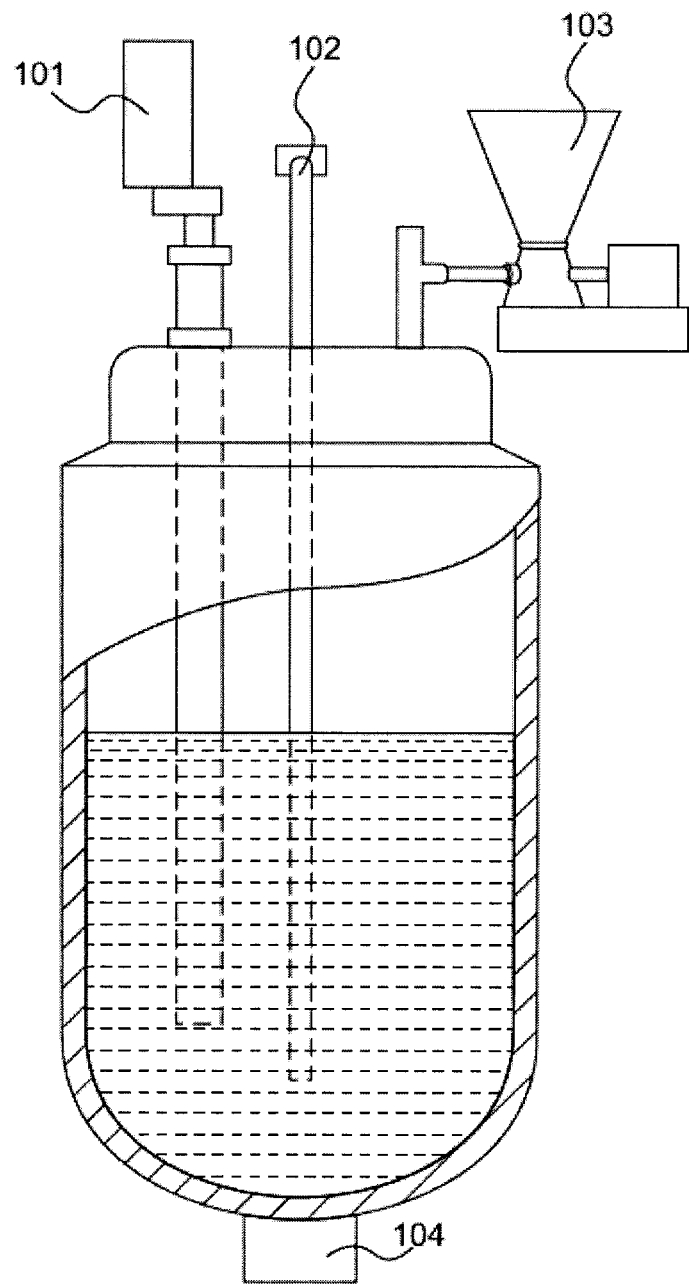
FIG. 3 is a partially broken away, perspective view of the process vessel of FIG. 2.
Figure 3A:
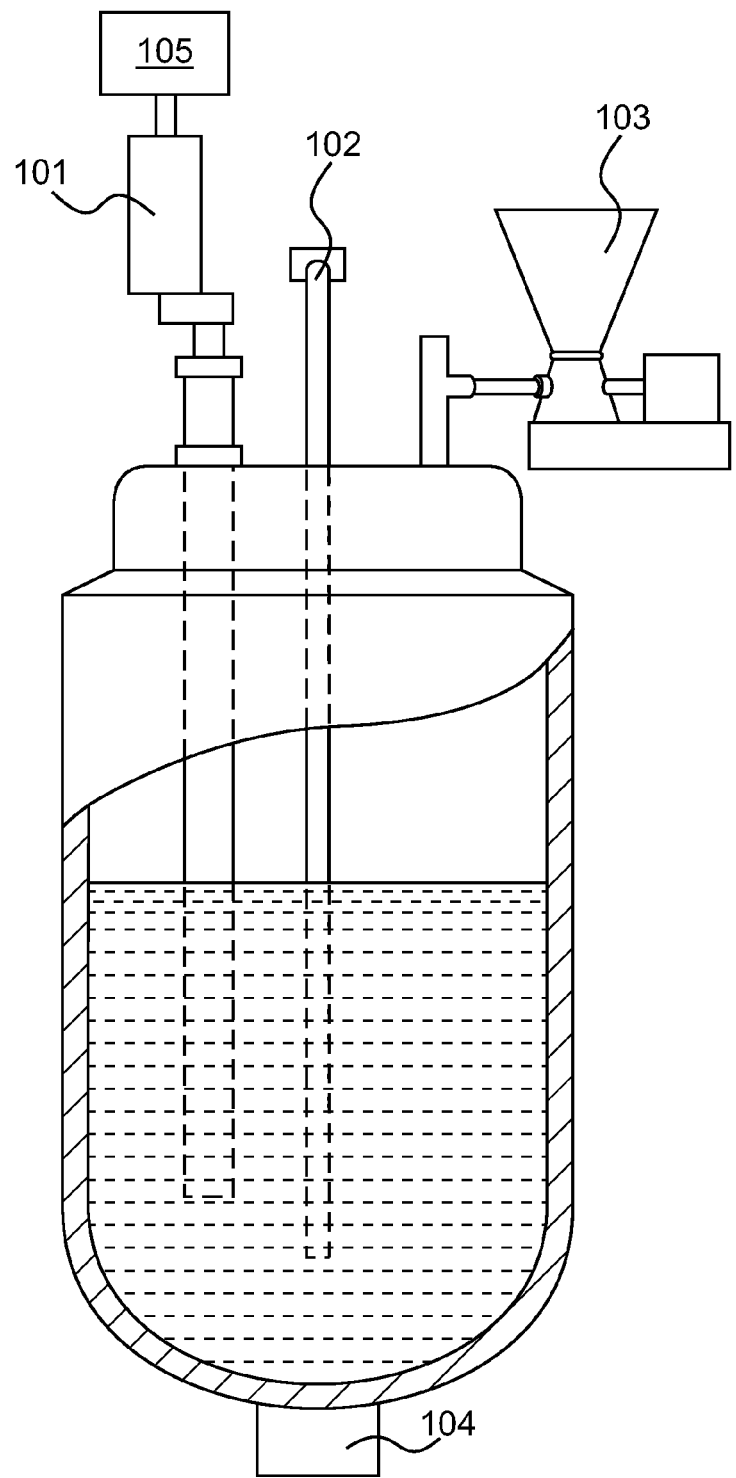
FIG. 3A illustrates an alternative embodiment similar to the process vessel shown in FIG. 3.

FIG. 3 illustrates in a partially broken away drawing of certain components of the process vessel 100 in FIG. 2. An agitator 101 can stir the contents of the process vessel. In some embodiments, the stirring can be according to a programmed agitation sequence. A dip tube 102 can extend into the process vessel and connect the circulating process stream back into the process vessel. The dip tube 102 can permit the circulating process stream to be added to the process vessel below the surface of the slurry or solution. The use of the dip tube 102 can also reduce foaming as the process stream returns to the process vessel. An inlet 103 can allow for the addition of dry ingredients. A tank outlet valve 104 can release the process stream from the process vessel to be directed to the circulating process stream pump 150 or the transfer tank filter 401 as controlled by valve 120. FIG. 3A illustrates an alternative embodiment of process vessel 100 as shown in FIG. 3 wherein controller 105 can be operatively connected to the agitator to control agitation.

The process of the invention can incorporate all of the individual operations of the conventional manufacturing process. The equipment for all of the operations can be contained within a single skid that can be moved to and located in a process room. The unit can be moved to another location. The process can be automated in a manner that eliminates or minimizes manual human intervention. Automated control over valve sequencing, pump settings, etc. can allow the process to flow automatically, eliminating the need for skilled operators. The system can be designed with specific cleaning sequences, spray devices, and pumps.

In one aspect of the invention, using at least one tangential flow filter in the filtration system 200 allows for continuous filtration as opposed to batch filtration. FIG. 4 shows a process flow of the filtration system 200 using at least one tangential flow filter. In certain embodiments, the at least one tangential flow filter can have a center channel through which the product stream flows. Small filtration pores through which the unwanted permeate (and not the product) flows can be perpendicular to the center channel and be directed to waste via valve 202. Suitable filters include hollow fiber filters, stainless steel filters, and ceramic filters. This tangential flow filtration system can permit the slurry to be pumped out of the process vessel, through the filter where a portion of the permeate can be removed, and the product slurry can then be returned to the tank. As the permeate is removed, solvent, e.g. water, can be added to the circulating process stream or process vessel to maintain a near constant tank volume. In various aspects of the invention, the solvent can be directed on an intermittent basis through the filtration pores in a reverse direction to the permeate stream via valve 201 while valve 202 is closed to remove any lodged materials from the pores, thereby maintaining an adequate permeate flow rate. This backwash process can also replace the volume of solvent lost as the permeate stream. The filtration system with backwash according to the invention can also be employed in a multiple filter arrangement (series, parallel, or series-parallel) and also in a multiple reaction vessel system where the filtration system can be used by intermittingly switching from one vessel to the next.

Figure 2A:
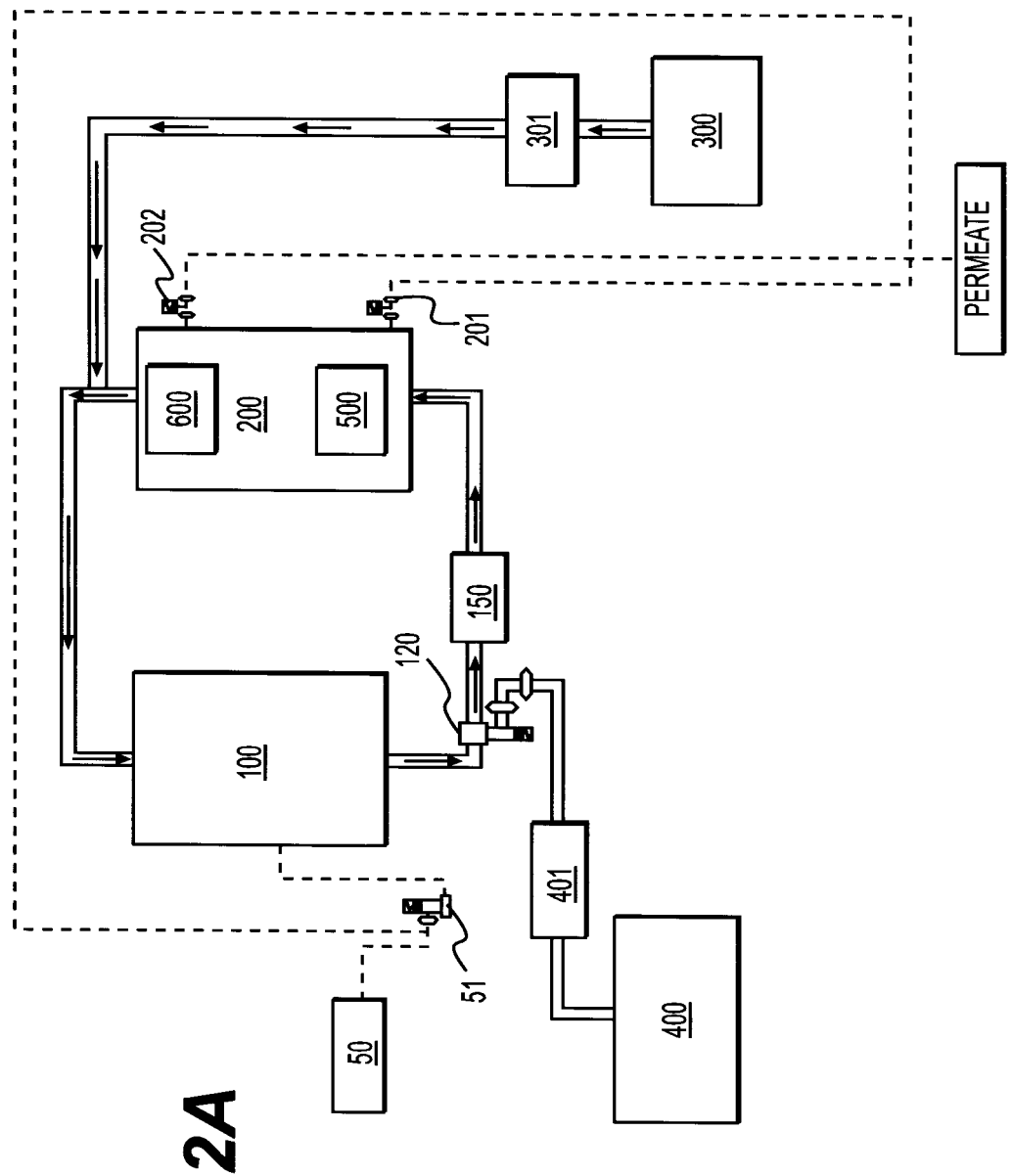
FIGS. 2A, 2B, and 2C illustrate alternative embodiments similar to the manufacturing apparatus shown in FIG. 2.

In certain embodiments, additional filters can be added in series to maintain an adequate permeate flow rate through the filtration system 200. FIG. 2A illustrates an alternative embodiment of the filtration system 200 wherein the filtration system contains two tangential flow filters 500 and 600 connected in series. It was anticipated that going from one to two filters would double the surface area and therefore maximally double the permeate flow rate and that going from one to three filters would triple the surface area and therefore maximally triple the permeate flow rate. Unexpectedly, it was discovered that the observed permeate flow rates in the continuous filtration process of the invention were more than double for two filters and more than triple for three filters, thereby increasing the effectiveness of tangential flow filtration when the filters are arranged in series. Increasing the diafiltration rate through the filtration system also can reduce the run time of the methods of the invention and thereby significantly reduce the shear on the product imposed by the product pump and agitator flow, etc., of the system. Example 3 describes the unexpected results.

From the Examples, one of skill in the art can design a batch or a continuous tangential flow filtration process using at least two filters arranged in series or in parallel. One of skill in the art could add, for example, 2, 3, 4, 5, 7, 10, or 50 filters or any number in between arranged in series or in parallel. The upper limit of additional filters added in series or parallel would be reached when the added filters introduce too much shear to the slurry and slow the permeate flow rate to an undesired level. Without wishing to be bound, we speculate that the additional filters in series add back pressure to the system to increase the pressure gradient across the filter to increase the permeate flow rate in a manner that does not create significant slurry particle shear. For a parallel array of filters, one of skill in the art may also need to increase the pipe size and pump capacity to maintain the flow rate due to the multiple flow paths necessary for a parallel array.

Figure 2B:
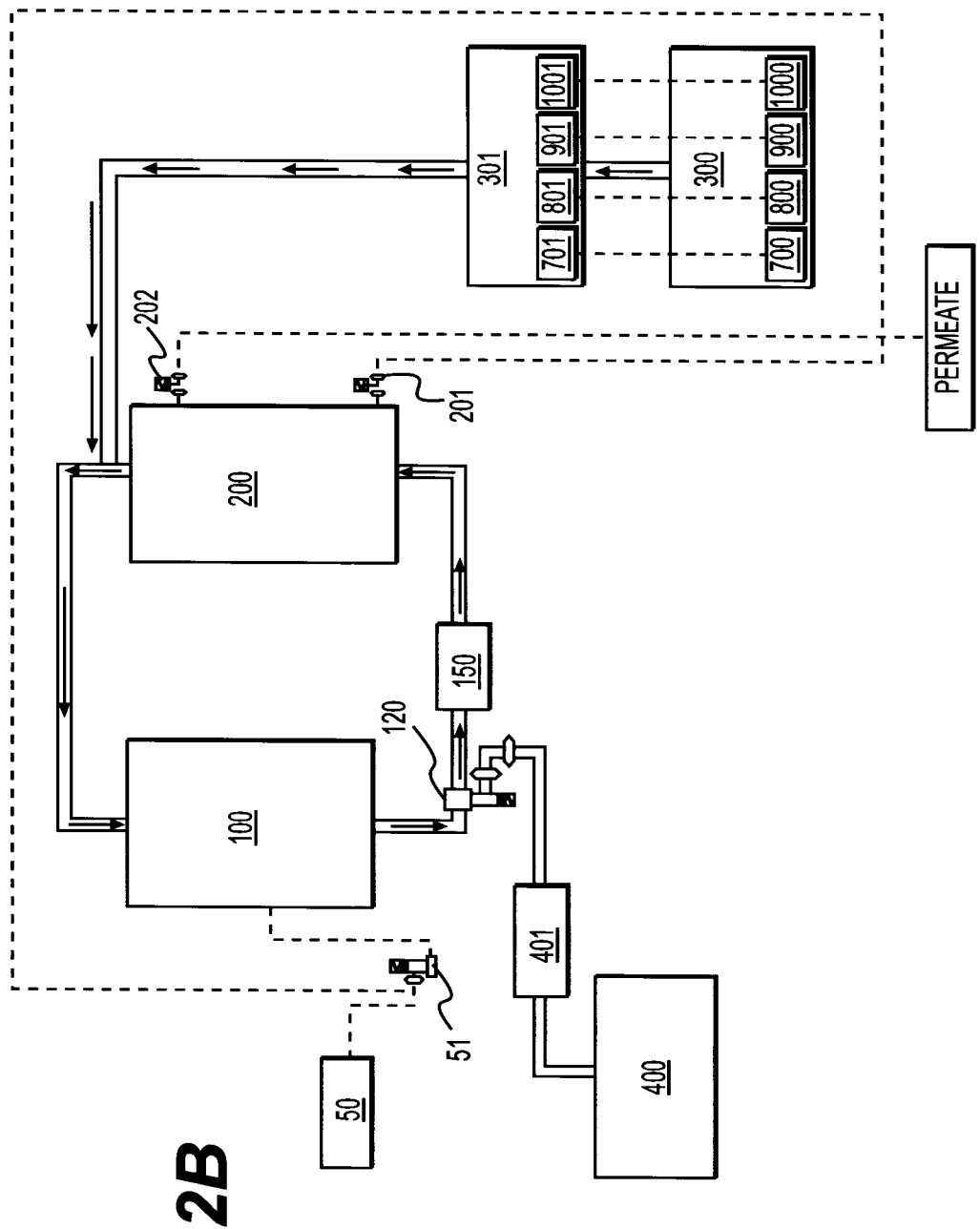
Figure 2C:
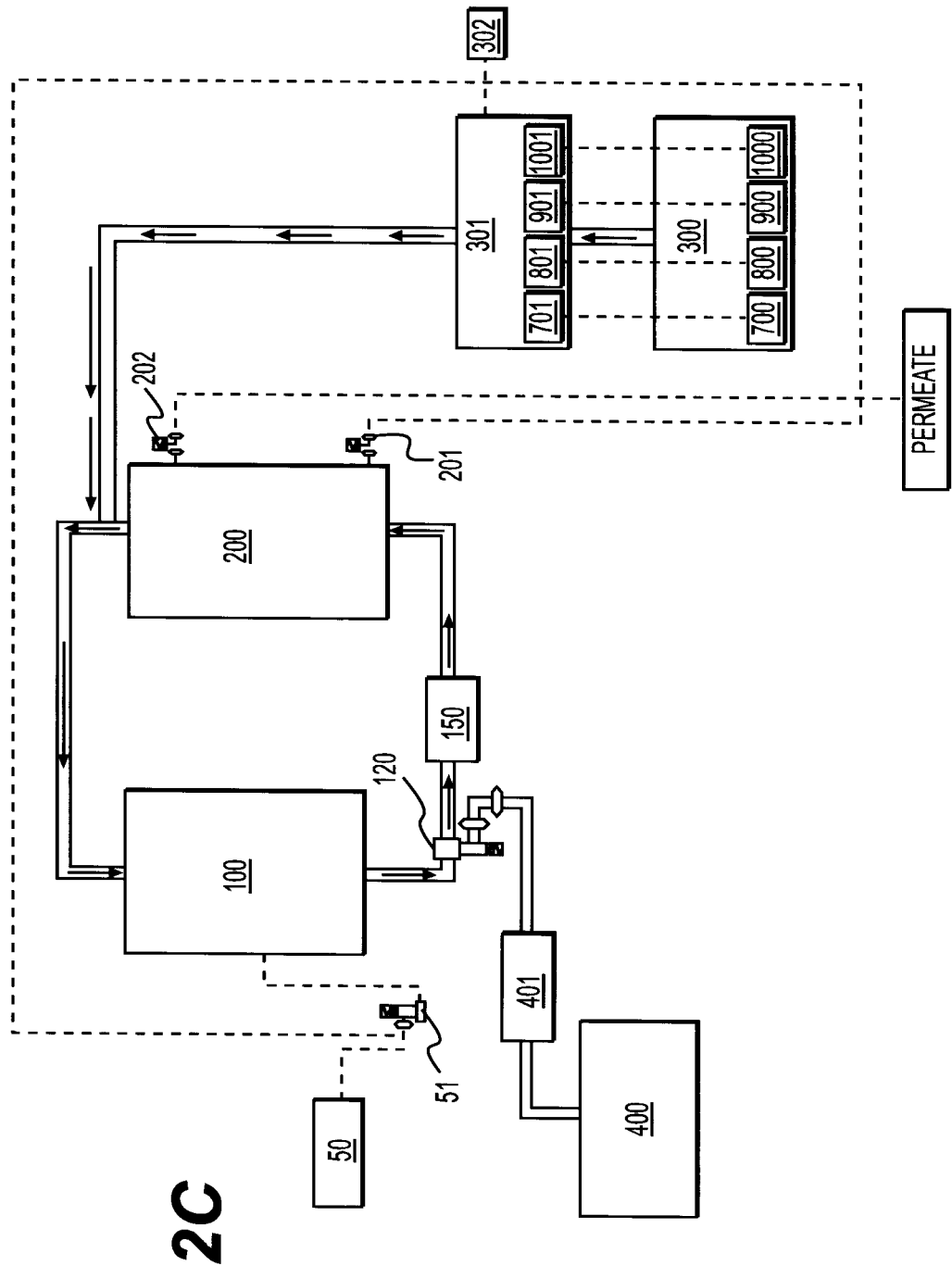

In another aspect of the invention, the addition system 300 can allow other chemicals to be introduced via one or more individual pumps 301 into the circulating process stream, as shown in FIG. 2. FIG. 2B illustrates an alternative embodiment of addition system 300 wherein the addition system contains four addition tanks 700, 800, 900, and 1000 each connected to a separate pump 701, 801, 901, and 1001. Pumps 701, 801, 901, and 1001 may each be connected to the circulating loop and independently configured to pump a chemical into the circulating process stream. FIG. 2C illustrates an alternative embodiment of FIG. 2B wherein controller 302 is operatively connected to addition pumps 701, 801, 901, and 1001 to control the addition of a chemical from each addition tank 700, 800, 900, and 1000 into the circulating loop. This approach can be used to introduce one or more chemicals. In certain embodiments, each chemical can be added via a separate pump into the circulating process stream after the process stream is filtered. In certain embodiments, each chemical can be added via a separate pump into the circulating process stream before the process stream is filtered. In certain embodiments, chemicals can be added via a separate pump into the circulating process stream both before and after the process stream is filtered. Chemicals added via an individual pump can include, for example, a base solution, a surfactant solution, an acid solution, or agents to adjust the pH. Additionally, this approach can be used to introduce cleaning chemicals for CIP.

Furthermore, the apparatuses and methods of the invention can minimize material handling and thereby can reduce the chance for inadvertent contamination as well as decrease exposure of the operators to the chemical reagents and products. For example, using a method according to the invention, there is no need to harvest the wet free base cake or to recharge it to an empty reaction vessel since the material can be maintained as a circulating slurry and processed as such. This minimization of material handling by the methods of the invention can result in increased and consistent yields nearing 100%. Yields from the conventional process range from 91 to 99% and typically average 95%. Conventional process yields vary from lot to lot in large part due to the variability of operator intervention.

The invention is further described by the following embodiments.

In one embodiment, the invention relates to an apparatus for preparing a solution of a shear sensitive material comprising:

a process vessel comprising an inlet for adding dry ingredients, an agitator, a dip tube, and a outlet valve;

a first pump connected to the outlet valve;

at least one tangential flow filter connected to both the first pump and the dip tube of the process vessel wherein the process vessel, the first pump, and the at least one tangential flow filter are configured to form a circulating loop; and at least one addition tank and at least one addition pump wherein the addition pump is configured to pump a reagent from the addition tank into the circulating loop.

In some embodiments, the dip tube can extend beneath the surface level of the contents contained within the process vessel.

In certain embodiments, the apparatus can comprise a controller to control agitation.

In various embodiments, the controller can be automated.

In some embodiments, the apparatus can comprise a controller to control the addition of a reagent from the addition tank into the circulating loop.

In certain embodiments, the controller can be automated.

In various embodiments, the addition pump can be configured to pump a reagent from the addition tank into the circulating loop after the at least one tangential flow filter.

In some embodiments, the apparatus can comprise a second valve and a transfer tank wherein the second valve is configured to control flow between the outlet valve and the transfer tank.

In certain embodiments, the apparatus can comprise a clarification filter between the second valve and the transfer tank.

In various embodiments, the apparatus can comprise at least two tangential flow filters wherein the filters are configured in series.

In some embodiments, the apparatus can comprise at least three tangential flow filters wherein the filters are configured in series.

In certain embodiments, the apparatus can comprise at least two addition tanks and at least two addition pumps wherein the first addition pump is configured to pump a first reagent from the first addition tank into the circulating loop and the second addition pump is configured to pump a second reagent from the second addition tank into the circulating loop and wherein the first addition pump is independent from the second addition pump.

In various embodiments, the apparatus can comprise at least three addition tanks and at least three addition pumps wherein the first addition pump is configured to pump a first reagent from the first addition tank into the circulating loop, the second addition pump is configured to pump a second reagent from the second addition tank into the circulating loop, and the third addition pump is configured to pump a third reagent from the third addition tank into the circulating loop and wherein each addition pump is independent from the other addition pumps.

In some embodiments, the apparatus can comprise at least four addition tanks and at least four addition pumps wherein the first addition pump is configured to pump a first reagent from the first addition tank into the circulating loop, the second addition pump is configured to pump a second reagent from the second addition tank into the circulating loop, the third addition pump is configured to pump a third reagent from the third addition tank into the circulating loop, and the fourth addition pump is configured to pump a fourth reagent from the fourth addition tank into the circulating loop and wherein each addition pump is independent from the other addition pumps.

In certain embodiments, the apparatus can comprise a liquid source connected to a liquid source valve wherein the liquid source valve is configured to control flow to the at least one tangential flow filter.

In various embodiments, the liquid source can be a water source.

In some embodiments, the liquid source valve can allow a liquid to flow through the pores of the at least one tangential flow filter into the circulating loop.

In certain embodiments, the liquid can be water.

In various embodiments, the invention relates to a process for preparing a solution of a shear sensitive material comprising:

a) adding a liquid to a shear sensitive material to form a slurry;

b) adding a first reagent to the slurry wherein the first reagent changes the properties or composition of the slurry;

c) passing the slurry containing the shear sensitive material through at least one tangential flow filter;

d) separating a filtrate from the slurry as a permeate stream by filtration;

e) adding a liquid to the slurry in an amount to replace at least some of the volume of liquid lost as the permeate stream; and f) adding a second reagent to the slurry wherein the second reagent changes the solubility of the shear sensitive material to yield a solution.

In some embodiments, the filtration can be continuous.

In certain embodiments, the filtration can be performed using at least two tangential flow filters in series.

In various embodiments, the filtration can be performed using at least three tangential flow filters in series.

In some embodiments, the liquid added in step e) can be added through the pores of the at least one tangential flow filter into the circulating stream.

In various embodiments, the amount of liquid added in step e) can be approximately equal to the volume of liquid lost as the permeate stream.

In certain embodiments, the liquid added can be water.

In various embodiments, reagents can be added through at least one pump into a circulating process stream.

In some embodiments, each reagent can be added by a separate pump pumping the reagent into the circulating process stream.

In certain embodiments, the invention relates to a process for preparing olanexidine gluconate comprising:

a) adding an aqueous base to an aqueous slurry of a salt of olanexidine;

b) passing the slurry containing olanexidine through at least one tangential flow filter;

c) separating a filtrate from the slurry of olanexidine as a permeate stream by filtration;

d) adding water to the slurry of olanexidine in an amount to replace at least some of the volume of water lost as the permeate stream; and e) adding a glucono-δ-lactone (gluconic acid) solution to the slurry of olanexidine to yield a first aqueous solution of olanexidine gluconate.

In various embodiments, the filtration can be continuous.

In some embodiments, the filtration can be performed using at least two tangential flow filters in series.

In certain embodiments, the filtration can be performed using at least three tangential flow filters in series.

In various embodiments, the aqueous base can be sodium hydroxide.

In some embodiments, the salt of olanexidine can be a hydrochloride salt.

In certain embodiments, the added water in step d) can be added through the pores of the at least one tangential flow filter into a circulating process stream.

In some embodiments, the amount of water added in step d) can be approximately equal to the volume of water lost as the permeate stream.

In various embodiments, the process can comprise adding water to the first aqueous solution to yield a second aqueous solution of olanexidine gluconate with a concentration ranging from about 0.1% to about 75% (W/V).

In some embodiments, reagents can be added through at least one pump into a circulating process stream.

In certain embodiments, each reagent can be added by a separate pump pumping the reagent into the circulating process stream.

In various embodiments, a surfactant solution can be added to the slurry of olanexidine after the water is added in step d).

In some embodiments, the invention relates to a process for preparing olanexidine gluconate comprising:

a) adding an aqueous sodium hydroxide solution to a first aqueous slurry of olanexidine hydrochloride;

b) passing the slurry containing olanexidine through at least one tangential flow filter;

c) separating a filtrate from the slurry of olanexidine as a permeate stream by filtration;

d) adding water to the slurry of olanexidine in an amount to replace at least some of the volume of water lost as the permeate stream;

e) adding a surfactant solution to the slurry of olanexidine to yield a second aqueous slurry; and f) adding a glucono-δ-lactone (gluconic acid) solution to the second aqueous slurry to yield a first aqueous solution of olanexidine gluconate.

In certain embodiments, the filtration can be continuous.

In various embodiments, the filtration can be performed using at least two tangential flow filters in series.

In some embodiments, the filtration can be performed using at least three tangential flow filters in series.

In certain embodiments, the surfactant solution can be a poloxamer solution.

In various embodiments, the added water in step d) can be added through the pores of the at least one tangential flow filter into a circulating process stream.

In certain embodiments, the amount of water added in step d) can be approximately equal to the volume of water lost as the permeate stream.

In some embodiments, the process can comprise adding water to the first aqueous solution to yield a second aqueous solution of olanexidine gluconate of a concentration ranging from about 0.1% to about 75% (W/V).

In certain embodiments, the concentration of the second aqueous solution can be about 6.95% (W/V).

In various embodiments, reagents can be added through at least one pump into a circulating process stream.

In some embodiments, each reagent can be added by a separate pump pumping the reagent into the circulating process stream.

In certain embodiments, the invention relates to a process for preparing olanexidine gluconate comprising:

a) adding an aqueous sodium hydroxide solution to a first aqueous slurry of olanexidine hydrochloride;

b) passing the slurry containing olanexidine through at least one tangential flow filter;

c) separating a filtrate from the slurry of olanexidine as a permeate stream by filtration;

d) adding water to the slurry of olanexidine in an amount to replace at least some of the volume of water lost as the permeate stream;

e) adding a poloxamer solution to the slurry of olanexidine to yield a second aqueous slurry;

f) adding a glucono-δ-lactone (gluconic acid) solution to the second aqueous slurry to yield a first aqueous solution of olanexidine gluconate; and g) adding water to the first aqueous solution to yield a second aqueous solution of olanexidine gluconate with a concentration ranging from about 0.1% to about 75% (W/V).

In various embodiments, the concentration of the second aqueous solution can be about 6.95% (W/V).

In some embodiments, the filtration can be continuous.

In certain embodiments, the filtration can be performed using at least two tangential flow filters in series.

In various embodiments, the filtration can be performed using at least three tangential flow filters in series.

In some embodiments, the added water in step d) can be added through the pores of the at least one tangential flow filter into a circulating process stream.

In various embodiments, the amount of water added in step d) can be approximately equal to the volume of water lost as the permeate stream.

In certain embodiments, reagents can be added through at least one pump into a circulating process stream.

In various embodiments, each reagent can be added by a separate pump pumping the reagent into the circulating process stream.

The following examples further illustrate how the processes of the invention can be conducted and evaluated, and are not intended to limit the scope of the invention, which is described in the claims. Unless indicated otherwise, parts are parts by weight and the temperature is in degrees C. or is at room temperature.

EXAMPLES

Example 1 describes a process for producing a 200 L nominal batch of 6.95% W/V $N^1$-(3,4-dichlorobenzyl)-$N^5$-octyl biguanide gluconate.

Example 1

A single tank was filled with 241 kg of purified water and an agitator was started. To this, 10.2 kg of $N^1$-(3,4-dichlorobenzyl)-$N^5$-octyl biguanide hydrochloride was added over approximately 50 minutes via an auger in a tube powder feeding device. The agitation was "pulsed" by briefly increasing the agitator speed to pull the powder from the gas-liquid interface down into the bulk liquid to create a slurry. Then, 24 kg of 40% (w/w) sodium hydroxide (NaOH) was introduced to the tank via the addition system. The sodium hydroxide solution was pumped into the recirculation loop by means of a peristaltic pump located on the skid. One of skill in the art would be able to substitute other strong aqueous bases. Examples of other strong aqueous bases include potassium hydroxide, calcium hydroxide, and barium hydroxide.

The resulting suspension was agitated in the tank for 60 minutes including intermittent agitation speed bursts wherein the rpm of the agitator was increased at approximately 40% for 20 seconds to yield a slurry containing $N^1$-(3,4-dichlorobenzyl)-$N^5$-octyl biguanide free base. Circulation of the slurry through the recirculation loop, which included three ceramic filters in series, was initiated. Each filter was approximately 100 centimeters in length and had pores of 5 micrometers. Each filter contained 19 center channels, each measuring 6 mm in diameter, for the slurry to pass through. The hydroxide and liberated chloride, along with water, were removed through the 5 micron pores in the filters forming the permeate stream during diafiltration of the product stream. Intermittent pulsed agitation continued. After the tank weight was reduced to 90% of the initial value via the permeate stream, water was added as a ceramic filter back flush to bring the tank weight back to the initial value. The back flush was achieved by directing the fresh water through the filter pores under high pressure in a direction counter to the normal permeate flow direction to facilitate filter pore regeneration. The amount of make-up water added was determined based on tank volume equivalents. Ten of the 10% replacements is equivalent to one tank volume being replaced. During diafiltration, six tank volumes (60×10% replacements) were replaced to reduce the hydroxide and chloride levels. After 6 tank volumes had been removed through the filters and the solution volumes replaced, the replacement was halted and water was removed from the slurry (dewatering) so that the slurry had a pre-determined mass (for example, 141.5 kg). The dewatering step allows for the addition of the poloxamer surfactant, gluconic acid, and water to achieve the nominal batch size of 200 L later in the process. The diafiltration and dewatering steps were accomplished in approximately 2 hours.

Ten kilograms of a Poloxamer 124 (also known as Pluronic® L44) surfactant solution were added to the dewatered (and dechlorinated) free base slurry containing $N^1$-(3,4-dichlorobenzyl)-$N^5$-octyl biguanide using a second peristaltic pump in the addition system. At the final batch volume, this will be equivalent to approximately 5% Poloxamer 124 W/V. One of skill in the art would be able to substitute another suitable nonionic surfactant solution following an evaluation of the reactivity of the surfactant solution with $N^1$-(3,4-dichlorobenzyl)-$N^5$-octyl biguanide, the surfactant's biological irritation potential, and its solubilizing ability.

Then, the initial charge of 11.5 kg of a 36% (w/w) aqueous gluconic acid solution was introduced into the recirculating slurry via a third peristaltic pump in the addition system, also located on the skid. The amount of gluconic acid added was 95% of the theoretical 1:1 molar equivalent relative to $N^1$-(3,4-dichlorobenzyl)-$N^5$-octyl biguanide. The poloxamer and initial gluconic acid were added over less than one hour and the resulting mixture was agitated until the resulting solution was clear. The pH was then adjusted to less than 5.2 with a target between 4.8 and 5.2 by adding gluconic acid through the same pump, although at a slower pump rate, into the recirculating clear stream. At this point in the process, the mass was made up to 95% of the final nominal batch size by first pushing the contents of the recirculation loop back into the tank using a stream of fresh water and then adding water until the desired weight of 190 kg was achieved.

Samples were withdrawn for in-process UV quantification. Each sample was diluted in an appropriate solvent. A standard of reference, $N^1$-(3,4-dichlorobenzyl)-$N^5$-octyl biguanide, was also prepared in the same solvent. The UV absorption of both the in-process sample and the standard was measured at 237 nm. The results were used to calculate the concentration of $N^1$-(3,4-dichlorobenzyl)-$N^5$-octyl biguanide with respect to the gluconate salt.

From the UV values measured at 95% of the nominal batch size, the yields were calculated to be typically 98-101% (The yield may occasionally be greater than 100% due to assay and weight measurement variability). These UV values were used to calculate the amount of water to be added to the tank to achieve a nominal product concentration of 6.95% (W/V). The resulting final product volume was typically 1-2% less than the nominal batch size of 200 L to account for the typical yield of 98-101%, sample pulls and volume losses associated with the final filtration hold up, etc. The water was added and the solution was agitated before it was discharged through a 0.45 micrometer pore size Nylon 66 clarification filter under moderate pressure into a storage tank. The material produced by the process of the invention would typically be further processed to produce the final drug product by means that have already been in practice. For example, the concentrate produced by the process of the invention may be diluted to the desired concentration, sterile filtered, and dispensed into final product containers.

Following the production run, a clean-in-place (CIP) sequence was carried out using a commercially available system such as hydroxyacetic acid with detergents (CIP-220®), potassium hydroxide solution with detergents (CIP-100®), and water rinses. The CIP solutions were introduced into the circulating cleaning stream via the reagent pumps of the addition system. The production rinse and cleaning processes were controlled by programs that use valve sequences to expose every relevant portion of the tank skid to the cleaning chemicals and water rinses at the recommended temperature for a specific amount of time. This cleaning process requires minimal operator interaction.

Example 2 describes a process for producing a 200 L nominal batch of 6.95% W/V $N^1$-(3,4-dichlorobenzyl)-$N^5$-octyl biguanide gluconate.

Example 2

A single tank is filled with 241 kg of purified water and an agitator is started. To this, 10.2 kg of $N^1$-(3,4-dichlorobenzyl)-$N^5$-octyl biguanide hydrochloride is added over approximately 50 minutes via an auger in a tube powder feeding device. The agitation is "pulsed" by briefly increasing the agitator speed to pull the powder from the gas-liquid interface down into the bulk liquid to create a slurry. Then, 24 kg of 40% (w/w) sodium hydroxide (NaOH) is introduced to the tank via a recirculation loop by means of a peristaltic pump on the skid.

The resulting suspension is agitated in the tank for 60 minutes including intermittent speed bursts to yield a slurry containing $N^1$-(3,4-dichlorobenzyl)-$N^5$-octyl biguanide free base. Circulation of the slurry through the recirculation loop, which includes three ceramic filters in series, is initiated. The hydroxide and liberated chloride, along with water, are removed through the 5 micron pores in the filters forming the permeate stream during diafiltration of the product stream. Intermittent pulsed agitation continues and water is added back to replace the water lost from the permeate stream. After the tank weight is reduced to 90% of the initial value via the permeate stream, water is added as a ceramic filter back flush to bring the tank weight back to the initial value. During diafiltration, six tank volumes (60×10% replacements) are replaced to reduce the hydroxide and chloride levels. After 6 tank volumes are removed through the filters and the solution volumes replaced, the replacement is halted and water is removed from the slurry (dewatering) so that the slurry has a pre-determined mass (for example, 141.5 kg). The diafiltration and dewatering steps are accomplished in approximately 2 hours.

Then, the initial charge of 11.5 kg of a 36% (w/w) aqueous gluconic acid solution is introduced into the recirculating slurry via a third peristaltic pump, also located on the skid. The initial gluconic acid is added over less than one hour and the resulting mixture is agitated until the resulting solution was clear. The pH is then adjusted to less than 5.2 with a target between 4.8 and 5.2 by adding gluconic acid through the same pump, although at a slower pump rate, into the recirculating clear stream. At this point in the process, the mass is made up to 95% of the final nominal batch size by first pushing the contents of the recirculation loop back into the tank using a stream of fresh water and then adding water until the desired weight of 190 kg is achieved.

Samples are withdrawn for in-process UV quantification. Each sample is diluted in an appropriate solvent. A standard of reference, $N^1$-(3,4-dichlorobenzyl)-$N^5$-octyl biguanide, is also prepared in the same solvent. The UV absorption of both the in-process sample and the standard is measured at 237 nm. The results are used to calculate the concentration of $N^1$-(3, 4-dichlorobenzyl)-$N^5$-octyl biguanide with respect to the gluconate salt.

From the UV values measured at 95% of the nominal batch size, the yields are calculated to be typically 98-101%. These UV values are used to calculate the amount of water to be added to the tank to achieve a nominal product concentration of 6.95% (W/V). The resulting final product volume is typically 1-2% less than the nominal batch size of 200 L to account for the typical yield of 98-101%, sample pulls, and volume losses associated with the final filtration hold up, etc. The water is added and the solution is agitated before it is discharged through a 0.45 micrometer pore size Nylon 66 clarification filter under moderate pressure into a storage tank. The material produced by the process of the invention would typically be further processed to produce the final drug product by means that have already been in practice. For example, the concentrate produced by the process of the invention may be diluted to the desired concentration, sterile filtered, and dispensed into final product containers. Following the production run, a clean-in-place (CIP) sequence, described in Example 1, is carried out.

Example 3

To maintain an adequate permeate flow rate through the filtration system, additional filters were added in series. It was anticipated that going from one to two filters would double the surface area and therefore double the permeate flow rate and that going from one to three filters would triple the surface area and therefore triple the permeate flow rate. This expectation represented the maximum increases and one of skill in the art would recognize that the actual permeate flow rates would be less due to non-ideal conditions including pressure losses, in particular across the second filter as created by the first filter.

Unexpectedly, it was discovered that the observed permeate flow rates in the continuous filtration process of the invention were in fact more than double for two filters and more than triple for three filters. Table 1 shows the representative results taken after 1 tank volume equivalent (ten water replacements of 10% of the tank volume each) has been diafiltered.

TABLE 1

Permeate Flow Rates Compared to Number of Filters in Series

| Number of Filters | Measured Permeate Flow Rate (liter/minute) | Multiple of Single Filter Result |
| --- | --- | --- |
| 1 | 5.5 | 1 |
| 2 | 20.6 | 3.7 |
| 3 | 25.6 | 4.6 |

The results show that for two filters in series the measured permeate flow rate was greater than triple the flow rate for a single filter. For three filters in series, the measured permeate flow rate was greater than quadruple the flow rate for a single filter. Without wishing to be bound, we speculate that the additional filters may provide additional backpressure and thereby increase the permeation rate, rather than causing a pressure loss as originally speculated.

Increasing the diafiltration rate through the filtration system also reduces the run time of the methods of the invention. Reducing the run time is significant for processing shear sensitive materials as the imposed shear is proportional to run time. Table 2 compares the times required for diafiltering and dewatering the slurry for one, two, and three filters in series for both 150 and 200 L batch sizes.

TABLE 2

Diafiltration and De-Watering Times for One, Two, and Three Filters in Series

| # Filters in Series | Batch Size (L) | Diafiltration Time (hrs) | De-Watering Time (hrs) | Total Time (hrs) |
| --- | --- | --- | --- | --- |
| 1 | 150 | 7 | 1.25 | 8.25 |
| 2 | 150 | 1.66 | .5 | 2.2 |
| 2 | 200 | 2 | 1 | 3 |
| 3 | 200 | 1.75 | 0.33 | 2.1 |

The invention has been described in detail with reference to the embodiments disclosed herein, but it will be understood that variations and modifications can be effected within the spirit and scope of the invention.

What is claimed is:

1. An apparatus for preparing a solution of a shear sensitive material comprising:
   a process vessel comprising an inlet to deliver dry ingredients to the interior of the process vessel, a dip tube extending into the interior of the process vessel to deliver a process stream to the interior of the process vessel, an agitator to stir the contents contained in the interior of the process vessel, and a outlet valve to release the process stream from the interior of the process vessel;
   a first pump connected to the outlet valve;
   at least two tangential flow filters connected in series wherein the first tangential flow filter is connected to the first pump and the last tangential flow filter is connected to the dip tube of the process vessel so that the process vessel, the first pump, and the at least two tangential flow filters are configured to form a circulating loop; and
   at least one addition tank connected to at least one addition pump wherein the addition pump is connected to the circulating loop and configured to pump a reagent from the addition tank into the circulating loop.

2. The apparatus of claim 1, further comprising a controller to control operation of the agitator.

3. The apparatus of claim 2, wherein the controller is automated.

4. The apparatus of claim 1, further comprising a controller operatively connected to at least one addition pump to control the addition of a reagent from the at least one addition tank into the circulating loop.

5. The apparatus of claim 4, wherein the controller is automated.

6. The apparatus of claim 1, wherein the at least one addition pump is connected to the circulating loop after the last tangential flow filter and before the dip tube of the process vessel.

7. The apparatus of claim 1, further comprising a second valve connected to the outlet valve and a transfer tank wherein the second valve is configured to control flow between the outlet valve and the transfer tank.

8. The apparatus of claim 7, further comprising a clarification filter between the second valve and the transfer tank.

9. The apparatus of claim 1, further comprising at least three tangential flow filters wherein the filters are connected in series.

10. The apparatus of claim 1, further comprising at least two addition tanks each connected to a separate addition pump wherein a first addition pump is connected to the circulating loop and configured to pump a first reagent from the first addition tank into the circulating loop and a second addition pump is connected to the circulating loop and configured to pump a second reagent from the second addition tank into the circulating loop and wherein the first addition pump is independent from the second addition pump.

11. The apparatus of claim 1, further comprising at least three addition tanks each connected to a separate addition pump wherein a first addition pump is connected to the circulating loop and configured to pump a first reagent from the first addition tank into the circulating loop, a second addition pump is connected to the circulating loop and configured to pump a second reagent from the second addition tank into the circulating loop, and a third addition pump is connected to the circulating loop and configured to pump a third reagent from the third addition tank into the circulating loop and wherein each addition pump is independent from the other addition pumps.

12. The apparatus of claim 1, further comprising at least four addition tanks each connected to a separate addition pump wherein a first addition pump is connected to the circulating loop and configured to pump a first reagent from the first addition tank into the circulating loop, a second addition pump is connected to the circulating loop and configured to pump a second reagent from the second addition tank into the circulating loop, a third addition pump is connected to the circulating loop and configured to pump a third reagent from the third addition tank into the circulating loop, and a fourth addition pump is connected to the circulating loop and configured to pump a fourth reagent from the fourth addition tank into the circulating loop and wherein each addition pump is independent from the other addition pumps.

13. The apparatus of claim 1, further comprising a liquid source connected to a liquid source valve wherein the liquid source valve is connected to the circulating loop and configured to control flow to the at least two tangential flow filters.

14. The apparatus of claim 13, wherein the liquid source is a water source.

15. The apparatus of claim 13, wherein the liquid source valve allows a liquid to flow through the pores of the at least two tangential flow filters into the circulating loop.

16. The apparatus of claim 15, wherein the liquid source is a water source.

17. The apparatus of claim 6, further comprising a controller operatively connected to at least one addition pump to control the addition of a reagent from the at least one addition tank into the circulating loop.

18. The apparatus of claim 17, wherein the controller is automated.

* * * * *